(12) United States Patent
Kim et al.

(10) Patent No.: US 7,390,658 B2
(45) Date of Patent: Jun. 24, 2008

(54) CD8α+LYMPHOID DENDRITIC CELL DIFFERENTIATED FROM HUMAN HEMATOPOIETIC STEM CELL AND A METHOD FOR DIFFERENTIATION

(75) Inventors: Hyun-Soo Kim, Dongshin Apt. 313-1003, #956-2, Youngtong-dong, Paldal-gu, Suwon-si, Kyungki-do (KR) 442-470; Kyung-Bock Lee, Sacheon-si (KR); Hugh-Chul Kim, Suwon-si (KR)

(73) Assignees: Lifecord, Inc. (KR); FCB-Pharmicell Co., Ltd. (KR); Hugh Chul Kim (KR); Hyun-Soo Kim (KR)

( * ) Notice: Subject to any disclaimer, the term of this patent is extended or adjusted under 35 U.S.C. 154(b) by 120 days.

(21) Appl. No.: 10/473,839

(22) PCT Filed: Mar. 28, 2002

(86) PCT No.: PCT/KR02/00544

§ 371 (c)(1),
(2), (4) Date: Feb. 19, 2004

(87) PCT Pub. No.: WO02/078599

PCT Pub. Date: Oct. 10, 2002

(65) Prior Publication Data

US 2004/0132185 A1    Jul. 8, 2004

(30) Foreign Application Priority Data

Mar. 29, 2001 (KR) .............................. 2001-16569

(51) Int. Cl.
*C12N 5/08* (2006.01)
(52) U.S. Cl. ........................................ 435/372; 435/377
(58) Field of Classification Search .................. None
See application file for complete search history.

(56) References Cited

U.S. PATENT DOCUMENTS 6,274,378 B1 * 8/2001 Steinman et al. ............. 435/377

OTHER PUBLICATIONS

Thirdborough et al, 1993, A method for the isolation of human lymphoid dendritic cells from the spleen. Transplant Immunology 1:143-145.*
Woolley et al., 2000, Mast cell activation and its relation to proinflammatory cytokine production in the rheumatoid lesion. Arth. Res. vol. 2: 65-74.*
Lardon et al., 1997, Generation of dendritic cells from bone marrow progenitors using GM-CSF, TNF, and additional cytokines: antagnoistic effects of IL-4 and IFN-gamma and selective involvement of TNF receptor-1. Immunology, vol. 91: 553-559.*
Lapointe et al., 2000, Human dendritic cells require multiple activation signals for the efficient generation of tumor antigen specific T lymphocytes. Eur. J. Immunol., vol. 30:3291-3298.*
Toshiaki Ohteki, et al., Interleukin 12-dependent Interferon γ Production by CD8a + Lymphoid Dendritic Cells, J. Exp. Med., vol. 189, No. 12, Jun. 21, 1999, p. 1981-1986.
Brian J. Czerniecki, et al., Calcium Ionophore-Treated Peripheral Blood Monocytes . . . , J. Immunol., 159 (1997) p. 3823-3837.
Marina Cella, et al., Current Opinion in Immunology 9(1) (1997) p. 10-16.

* cited by examiner

*Primary Examiner*—G. R. Ewoldt
*Assistant Examiner*—Amy E Juedes
(74) *Attorney, Agent, or Firm*—Baker & Hostetler, LLP

(57) ABSTRACT

Lymphoid dendritic cells with immunophenotype CD8α+ can be produced by a method which comprises culturing human hematopoietic stem cells in a medium containing GM-CSF, followed by culturing in a medium containing IFN-Y, the lymphoid dendritic cells being useful in various immunotherapies.

4 Claims, 9 Drawing Sheets

CD3

CD3

CD8α⁺LYMPHOID DENDRITIC CELL DIFFERENTIATED FROM HUMAN HEMATOPOIETIC STEM CELL AND A METHOD FOR DIFFERENTIATION

FIELD OF THE INVENTION

The present invention relates to lymphoid dendritic cells differentiated from human hematopoietic stem cells, a method for differentiating the lymphoid dendritic cells from human hematopoietic stem cells and a pharmaceutical composition for immunotherapy containing the lymphoid dendritic cells as an active ingredient.

BACKGROUND OF THE INVENTION

Dendritic cells (DCs) are powerful antigen presenting cells (APCs) that orchestrate various immune responses against specific antigens and at the same time suppress auto-immune response by deleting potentially autoreactive T cells. These apparently contradictory functions have been suggested to originate from different subsets of DCs.

Murine DCs can be subdivided into at least two distinct subtypes, myeloid and lymphoid DCs, on the basis of their anatomic localization, transplantation experiments, and cell surface phenotypes. DCs bearing the $CD11c^+$, $MHCII^+$, $CD4^+$, $CD8\alpha^-$ cell surface phenotype, called $CD8\alpha^-$ myeloid DCs, can be derived from myeloid precursor cells, whereas DCs bearing the $CD11c^+$, $MHCII^+$, $CD4^-$, $CD8\alpha^+$ cell surface phenotypes, called $CD8\alpha^+$ lymphoid DCs, are present in thymus or spleen.

It has been reported that murine $CD8\alpha^+$ lymphoid DCs also produce IFN-γ in response to IL-12 like NK cells(natural killer cells) and T cells (Toshiaki et al., *Brief Definitive Report*, 189(12), 1981-1986(1999)), Also, when lymphoid DCs such as murine Langerhans cells are injected into $CD8\alpha^-$ mice, they are transferred into the lymph node and differentiate into $CD8\alpha^+$ DCs and the differentiated $CD8\alpha^+$ DCs can produce IFN-γ (Miriam et al., *Blood*, 96(5), 1865-1872(2000)).

Such lymphoid DCs not only induce immune tolerance but function as powerful immunogenic APCs against various allogeneic antigens, activating T helper cell type I response by producing IL-12 and IFN-γ.

DCs are present virtually in all tissues of the body, but in low concentrations, and it is therefore difficult and cumbersome to procure a sufficient amount of DCs for ex vivo manipulation.

Accordingly, various efforts have been made to generate DCs ex vivo from HSCs or monocytes in a large scale, using for example, several cytokines including Granulocyte-macrophae colony stimulating factor (GM-CSF), interleukin-4 (IL-4), tumor necrosis factor-alpha (TNF-α) and stem cell factor (SCF). DCs which express $CD1a^+$, $CD4^+$, $CD11c^+$, $CD40^+$, $CD54^+$, $CD80^+$, $CD83^+$, $CD86^+$, HLA class I⁺, HLA class II⁺, $CD3^-$, $CD8^-$ and $CD14^-$ were generated by using GM-CSF (Williams et al., *Int. Rev. Cytol.*, 153: 412(1994); Santiago-Schwarz et al., *Nature*, 360: 258(1993); and Rosenzwajg et al., *Blood*, 87: 535(1996)).

However, it has never been reported that DCs of $CD8\alpha^+$ immunophenotype ($CD8\alpha^+$ DCs) are present in human or that $CD8\alpha^+$ DCs can be differentiated from human hematopoietic stem cells(HSCs).

SUMMARY OF THE INVENTION

Accordingly, it is a primary object of the present invention to provide a lymphoid dendritic cells of a $CD8\alpha^+$ immunophenotype which are differentiated from human hematopoietic stem cells.

It is another object of the present invention to provide a method for differentiating the lymphoid dendritic cells from human hematopoietic stem cells.

It is still another object of the present invention to provide a pharmaceutical composition for immunotherapy comprising the lymphoid dendritic cells.

It is a further object of the present invention to provide a method for treating an immune-related disease in a mammal.

In accordance with one aspect of the present invention, there is provided lymphoid dendritic cells of $CD8\alpha^+$ immunophenotype of which are differentiated from human hematopoietic stem cells.

In accordance with another aspect of the present invention, there is provided a method for differentiating the lymphoid dendritic cells which comprises culturing human hematopoietic stem cells in two steps, first in a first medium containing GM-CSF and then in a second medium containing IFN-γ.

In accordance with another aspect of the present invention, there is provided a pharmaceutical composition for immunotherapy which comprises a therapeutically effective amount of the dendritic cells.

In accordance with still another aspect of the present invention, there is provided a method for treating an immune-related disease in a mammal, which comprises administering the lymphoid dendritic cells to a subject in need thereof in an amount effective for treating the disease.

BRIEF DESCRIPTION OF THE DRAWINGS

The above and other objects and features of the present invention will become apparent from the following description of the invention taken in conjunction with the following accompanying drawings, wherein.

DETAILED DESCRIPTION OF THE INVENTION

Figure 1A:
FIGS. 1A, 1B and 1C: light microscope(A), scanning electron microscope(B) and transmission electron microscope(C) photographs of lymphoid dendritic cells differentiated from human hematopoietic stem cells.

The CD8α+ lymphoid dendritic cells of the present invention have immunophenotypes of CD1a−, CD3−, CD4−, CD8+, CD11c+, CD14−, CD40+, CD54+, CD80+, CD83+, CD86+, HLA-I+ and HLA-II+.

The CD8α+ lymphoid dendritic cells can be prepared by culturing hematopoietic stem cells in two steps, first in a first medium containing GM-CSF (granulocyte macrophage-colony stimulating factor) for an appropriate period, e.g., 3 to 9 days, and then in a second medium containing IFN-γ (interferon-γ), e.g., for 3 to 9 days.

In the inventive process, GM-CSF and IFN-γ may be added to the medium every 2-4 days, preferably 3 days, in amounts ranging from 1 to 1,000 ng/ml and from 1 to 1,000 U/ml, respectively, preferably, 20 to 200 ng/ml and 50 to 500 U/ml, respectively.

In order to enhance the differentiation of mature DCs, it is preferred to add ionomycin, lipopolysaccharide (LPS) or keyhole limpet hemocyanin (KLH) to the second medium in an amount of 0.1 to 10 µg/ml, preferably 1 µg/ml, on the later part of the second stage culture and culture until the end of the second culture period, preferably for 1 day.

The CD8α+ lymphoid dendritic cells of the present invention have advantages in that: interleukin-12 and IFN-γ can be produced in high yields; T cells can be stimulated into proliferation; and powerful cellular immune responses can be induced by activating T helper cells and cytotoxic T lymphocyte.

The CD8α+ lymphoid dendritic cells of the present invention can be used as an active ingredient of a pharmaceutical compostion for an immunotherapy for a immune-related disease. Non-limiting examples of immune-related diseases, which can be treated by using the CD8α+ lymphoid dendritic cell of the present invention, include any kind of malignant diseases, tuberculosis infections, HIV infections and autoimmune diseases.

A pharmaceutical composition for preventing or treating immune-related diseases can be prepared by mixing the inventive CD8α+ lymphoid dendritic cells with a pharmaceutically acceptable excipient or carrier, or by diluting it with a pharmaceutically acceptable diluent in accordance with any of the conventional procedures. Examples of suitable carriers, excipients, and diluents are lactose, dextrose, sucrose, sorbitol, water, and mineral oil. The formulations may additionally include fillers, anti-agglutinating agents, preservatives and the like. The pharmaceutical composition of the present invention may be formulated so as to provide quick, sustained or delayed release of the active ingredient after their administration to a mammal by employing any of the procedures well known in the art. Thus, the formulations may be in the form of a sterile injectable solution, suspension, emulsion, solution and the like, wherein a sterile injectable solution is preferred.

Accordingly, the present invention also provides a method of treating an immune-related disease in a mammal, which comprises administering the inventive CD8α+ lymphoid dendritic cells to a subject in need thereof in an amount effective for treating the disease.

The inventive CD8α+ lymphoid dendritic cells may be administered to a patient by the conventional immunotherapy methods. Specifically, auto-cells are taken from the patient and cultured to obtain DCs having an immunological enhancement effect and the DCs are pulsed with a target antigen. In this process, in order to increase the immunological enhancement effect of DCs, the DCs may be pulsed in the presence of radiation or ultraviolet-treated cancer cells, a lysate of cancer cells killed by freezing-thawing or a cytotoxic drug. Another method is to pulse DCs using a DNA, RNA, protein or peptide as an antigen. The DCs pulsed with a specific antigen may be directly injected into a patient, or T cells activated by the inventive DCs may be injected. Further, to enhance therapeutic effects, it is preferred to inject the inventive DCs together with IL-2.

The cell composition of the present invention can be administered via various routes including transdermal, subcutaneous, intravenous and intramuscular introduction, and direct injection into cancerous regions.

Typical unit dose of the CD8α+ lymphoid dendritic cells may range from $1 \times 10^7$ to $1 \times 10^9$ cells and they can be administered weekly or monthly for 6 months. However, it should be understood that the amount of the active ingredient actually administered ought to be determined in light of various relevant factors including the disease to be treated, the severity of the patient's symptom, the chosen route of administration, and the age, sex and body weight of the individual patient; and, therefore, the above dose should not be intended to limit the scope of the invention in any way.

The immunotherapy using the inventive pharmaceutical composition is advantageous in that the immunologic rejection does not occur due to the use of the dendritic cells differentiated from the patient's hematopoietic stem cells and also in that the dendritic cells injected into the body can continuously produce cytokines.

The inventive pharmaceutical composition induces a strong cellular immuno-response against diseases caused by specific antigens, stimulating T cell proliferation, and it can be advantageously used in anti-cancer and anti-virus therapies.

The following Examples are intended to further illustrate the present invention without limiting its scope; and the experimental methods used in the present invention can be practiced in accordance with Examples given herein below, unless otherwise stated.

Further, percentages given below for solid in solid mixture, liquid in liquid, and solid in liquid are on the bases of wt/wt, vol/vol and wt/vol, respectively, unless specifically indicated otherwise.

EXAMPLE 1

Extraction of Hematopoietic Stem Cell and Generation of Dendritic Cell

In order to mobilize peripheral blood stem cells (PBSCs), granulocyte colony stimulating factor (G-CSF, Lenograstim, chugai, Co., Tokyo, Japan) were injected subcutaneously into 10 patients with various neoplastic diseases (breast cancer, leukemia and lymphoma) at a dose of 300 µg/day, respectively. Peripheral blood stem cells were extracted in accordance with leukapheresis using Cobe Spectra (Cobe BCT, Inc., Lakewood, Colo., USA) cell separator on day 4 after in the injection. Mononuclear cells were separated from the peripheral blood stem cells thus obtained in accordance with the density gradient centrifugation method using Ficoll-Hypaque (Histopaque, Sigma Chemical, St. Louis, Mo., USA) and washed twice with phosphate buffered saline (PBS, Sigma Chemical). The mononuclear cells filtered with a 30 µm nylon mesh membrane in PBS containing 5% bovine serum albumin (BSA). Mononuclear cells were collected, added FcR blocking reagent, reacted with CD34 microbeads (Miltenyi Biotec GmbH) at 4° C. for 30 minutes, washed with PBS containing BSA, passed cells through mesh and CD34+ mononuclear cells were separated by conducting high gradient immunomagnetic separation (HGIS; MidiMACS, Miltenyi biotech, USA). $1\times10^5$/ml of the separated CD34+ peripheral blood stem cells were cultured in X-VIVO 20 medium (Biowhittaker, Walkersville, Md., USA) with 5% human serum albumin, 100 U/ml of penicillin, 100 µg/ml of streptomycin (Sigma), 100 U/ml of L-glutamine (Sigma) for 2 weeks, while adding 50 ng/ml of GM-CSF (Leucogen, LG Chemical Co., Korea) every three days during the first week, followed by adding 200 U/ml of IFN-γ (Intermax-γ, LG Chemical Co., Korea) every three days during the second week. On day 13, i.e., the day before the end of the second week, 1 µg/ml of ionomycin (Sigma) was added to the medium and cultured for 1 day to allow the cells to mature.

Figure 1B:
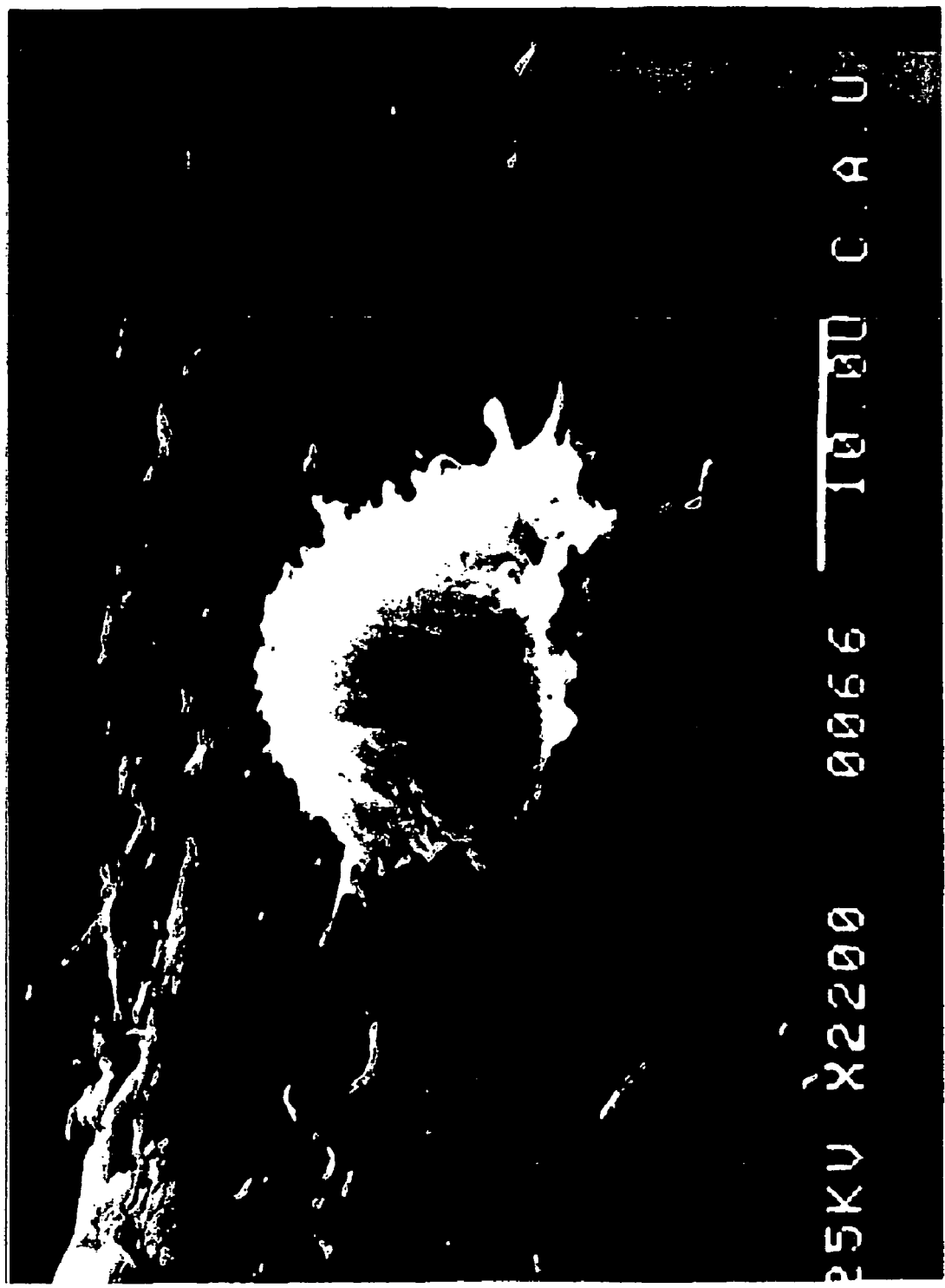
Figure 1C:

As shown in FIG. 1, the cultured cells have relatively abundant cytoplasm with multiple dendrites (Giemsa-Wright stain). The cells colonized and conglomerated on the surface of the culture flask during the early phase of culturing but started to separate and proliferate when IFN-γ was added on the second week of culturing. Further, as can be seen in the scanning and transmission electron micrographs, the cells reveal the DCs' characteristic features: the nucleus is shifted to one side of the region; multiple dendrites are present on the cell surface; and the abundant cytoplasm has many granules.

On the other hand, in order to examine the culture time-dependant enhancement in the dendritic cell count, 1 ml samples of the culture solutions after 1 week and 2 weeks were examined with hemocytometer.

Figure 2:
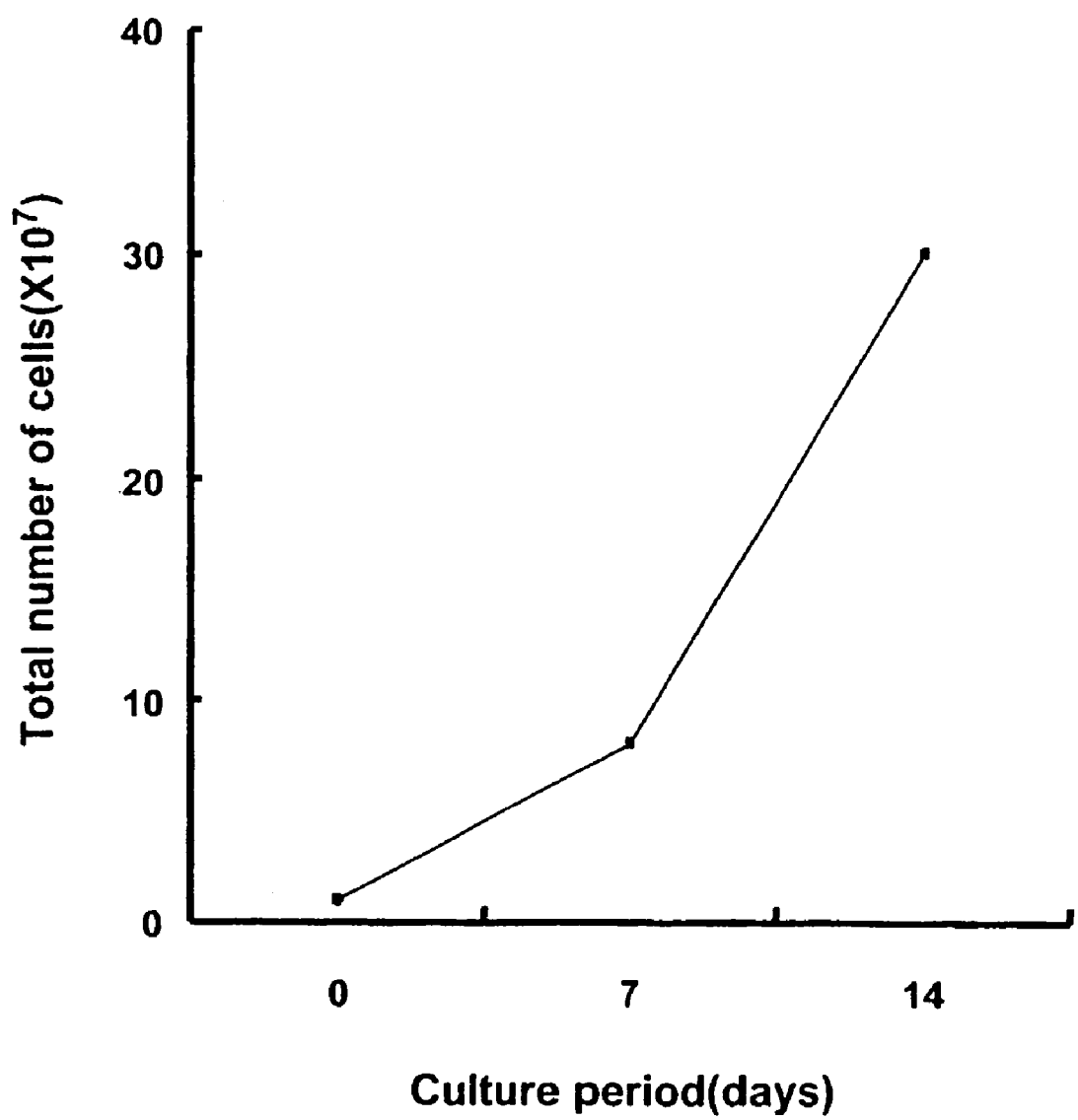
FIG. 2: the culture time-dependent change of the dendritic cell count.

As shown in FIG. 2, the total cell count increased continuously throughout the culture period, especially after adding IFN-γ. On day 14, the last day of culturing, the cell count was about $30\times10^5$/ml, about 30 times higher than the initial cell count.

EXAMPLE 2

Examination of Immunophenotype of the Differentiated DCs

To confirm the immunophenotype of the cultured DCs, $1\times10^5$ of cells were reacted with fluorescein isothiocyanate or phycoerythrin-labeled specific monoclonal antibodies for CD1a, CD3, CD4, CD8α, CD11c, CD14, CD80, CD83, CD86, HLA class I(ABC), and HLA class II(DR) (Pharmingen, San diego, Calif., USA) in PBS containing 5% FBS (fatal bovine serum) at room temperature for 15 minutes in the dark room, and the resulting solution was washed with PBS, and then analyzed by flow cytometry (FACScan, Becton Dickinson).

Figure 3:
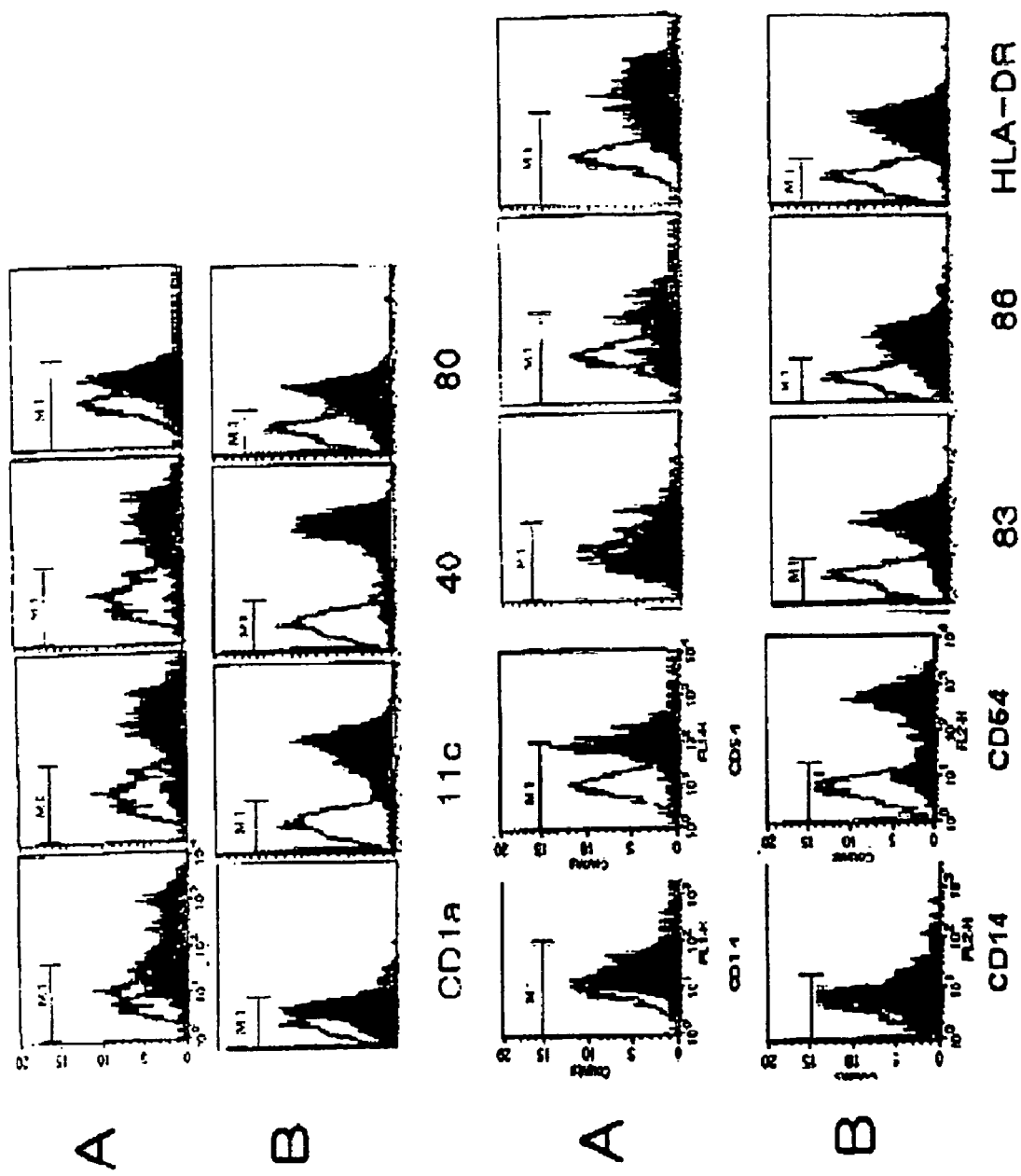
FIGS. 3A and 3B: histograms showing the immunophenotye of the lymphoid dendritic cells (A: a cell after culturing for 7 days; B: a cell after culturing for 14 days; x axis: cell count; y axis: fluorescent intensity; open histogram: a negative control; and filled histogram: a positive cell group for cell surface antigen)
Figure 4A:
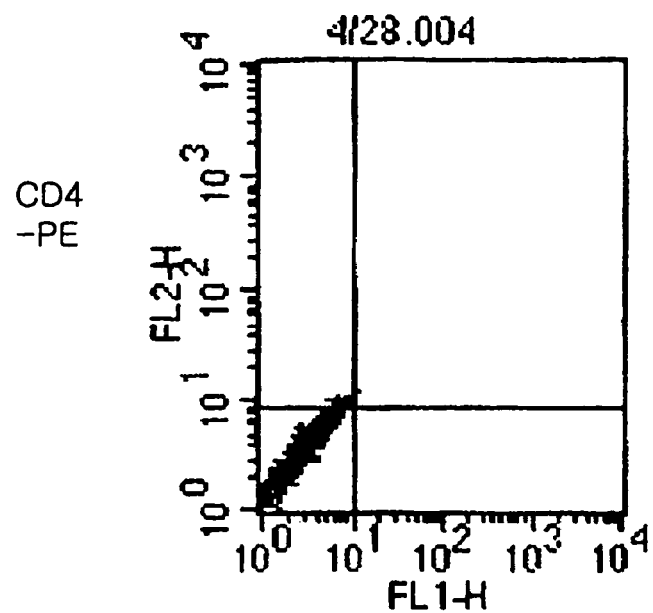
FIGS. 4A and 4B: histograms showing the immuno phenotye of the lymphoid dendritic cells(A: only CD3 and CD4 are stained, and B: only CD3 and CD8α are stained)
Figure 4B:
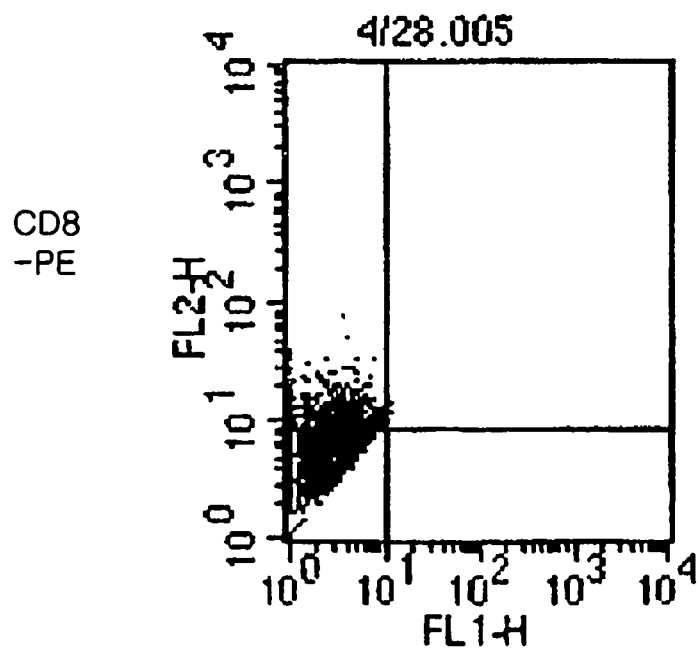

As shown in the FIGS. 3A and 3B, on day 7 of the culture, the cells expressed CD1a, CD11c as well as CD40, CD54, CD80, CD86 and HLA class I/II. However, CD83+, a maker for mature DCs, expressed weakly. The addition of ionomycin altered the CD1a and CD14 into the negative phenotypes and the cells of CD83+ phenotype increased. Further, as shown in the FIGS. 4A and 4B, the cells exhibited negative phenotypes of CD3 and CD4, while CD8α phenotype was positive.

These results suggested that the lymphoid dendritic cells differentiated from human hematopoietic stem cells are lymphoid DCs that express CD1a−, CD3−, CD4−, CD8α+, CD11c+, CD14−, CD40+, CD54+, CD80+, CD83+, CD86+, HLA-I+ AND HLA-II+ and, most interestingly, CD8α+.

EXAMPLE 3

Confirmation of the Phagocytic Ability of CD8α+ DCs

To confirm the phagocytic ability of the differentiated DCs, $2\times10^5$ of DCs was mix-incubated with dextran-FITC (Sigma) at 37° C. for 1 hour without FBS. Then, the dextran engulfed cells were examined by a flow cytometry.

Figure 5A:
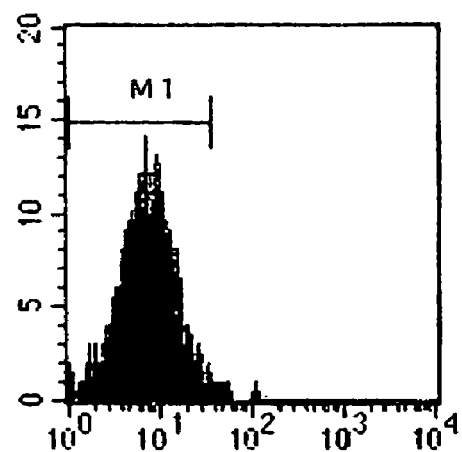
FIGS. 5A, 5B and 5C: the ability to phagocytize FITC-labeled dextran (A: a control; B: a cell group after culturing for 1 week; C: a cell group after culturing for 2 weeks; open histogram: a negative control and filled histogram: a cell group which phagocytize FITC-labeled dextran)
Figure 5B:
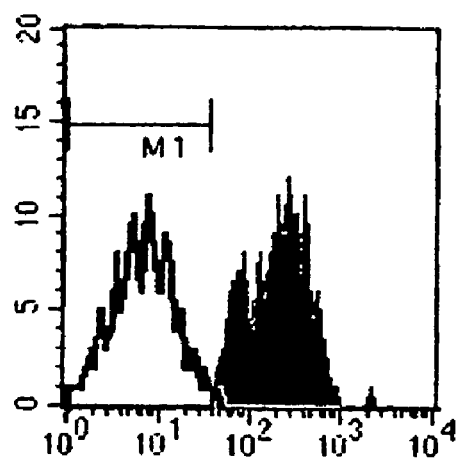
Figure 5C:
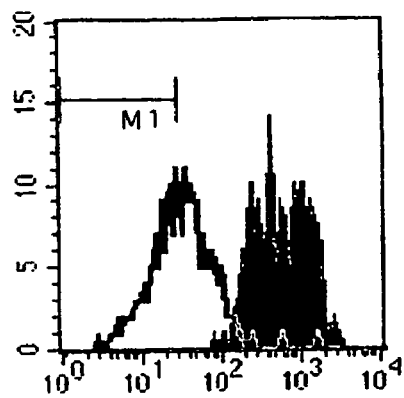

As shown in the FIGS. 5B and 5C, CD8α+ CDs had high phagocytic activity. Further, on day 14 of the culture, the phagocytic activity was further augmented. A control experiment at 4° C. (5A) showed the observed phagocytic activity of the inventive CD8α+ CDs is real, not an artifact created by measurement conditions.

EXAMPLE 4

Examination of Inducting Ability of CD8α+ DCs in Lymphocyte Proliferation

To examine the ability of DCs in stimulating T cell proliferation, allogeneic mixed lymphocyte reaction (MLR) was carried out as follows.

Peripheral mononuclear cells (MNCs) were isolated from normal volunteer's blood in accordance with the density gradient centrifugation method using Ficoll-Hypaque (Histopaque; Sigma Chemical, St. Louis, Mo., USA) and washed with PBS. $3\times10^8$ of MNC thus obtained were incubated in a human T cell enrichment column (R & D, USA) at room temperature for 10 minutes and T cells were extracted with PBS. Then, γ-ray irradiated(30 Gy) DCs and T cells (effector: responder) were added to the microplate in varying ratios of 1:1, 1:10, $1:10^2$, $1:10^3$ and $1:10^4$, in triplicates, and then, incubated at 37° C. for 3 days. 20 µl of BrdU(5-bromo-2'-deoxyuridine) was added thereto and further incubated for 24 hours. Formaldehyde was added to the plate and reacted at room temperature for 30 minutes to fix the cells, 100 µl of an anti-BrdU solution was added to the plate, and allowed to react at room temperature for 90 minutes. Then, the plate was washed with PBS and reacted with a color development-substrate for 30 minutes. 1N $H_2SO_4$ was added thereto to stop the reaction and the absorbance at 450 nm was measured with ELSA plate reader (Molecular device, USA).

Figure 6:
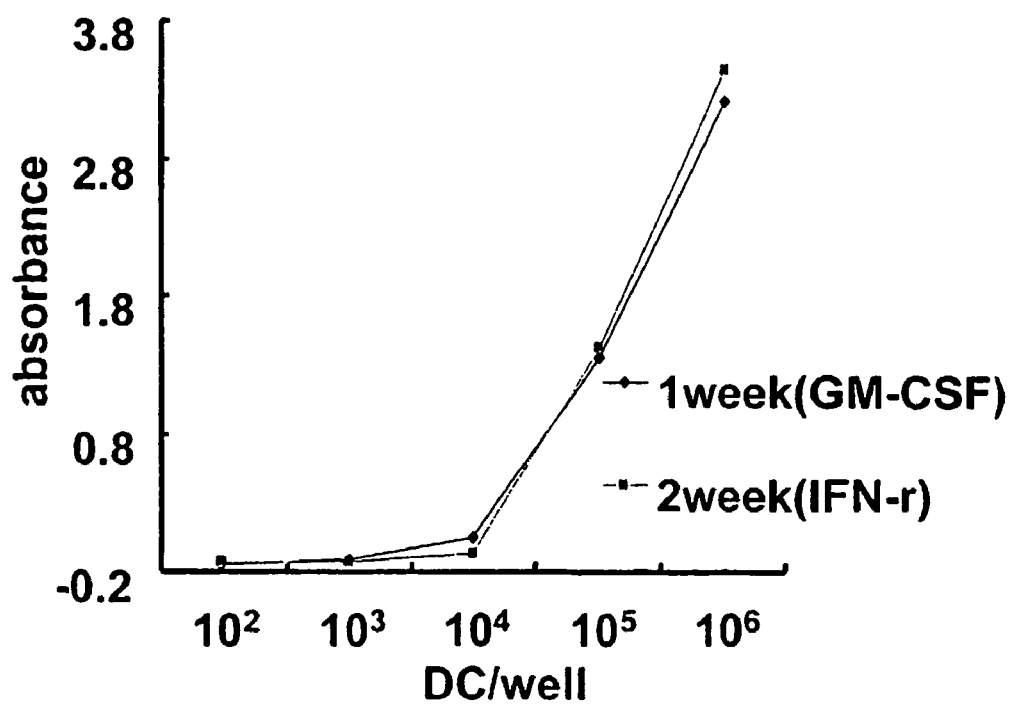
FIG. 6: the ability to stimulate T-cell proliferation (♦: a cell group after culturing for 1 week and ■: a cell group after culturing for 2 weeks)

As the result in FIG. 6 shows, a burst of T cell proliferation was observed at a ratio of $1:10^4$ (effector:responder). This demonstrates that the lymphoid DCs are functionally capable of stimulating the proliferation of the T lymphoid.

EXAMPLE 5

Determination of Cytokine Release of Lymphoid DCs

The cells' cytokine releasing capability was measured by ELISA(enzyme-linked immunosorbant assay) as follows.

An anti-human IL-12 and IFN-γ antibodies(Pharmingen) were diluted in 0.1 mol/l of $NaHCO_3$ to 2 µg/ml, and 50 µl of the resulting solution was divided to the ELISA plate(Corning) to be incubated at 4° C. for 24 hours. PBS containing 5% FBS was added to block the plate for 3 hours. 50 µl of a standard sample and 50 µl each of the culture solutions at day 7, 13 and 14 of the culture were added thereto and reacted for 4 hours.

2 µg/ml of Biotin-conjugated detection antibody was added to the plate and reacted for 3 hours. The plate was washed, treated with a streptavidin-horseradish peroxidase solution (diluted to 1:2000) for 1 hour, washed again, and then treated with TMB (Zymed, San Francisco, Calif., USA), followed by measuring the absorbance at 450 nm using ELISA microplate reader(Molecular device, USA).

Figure 7A:
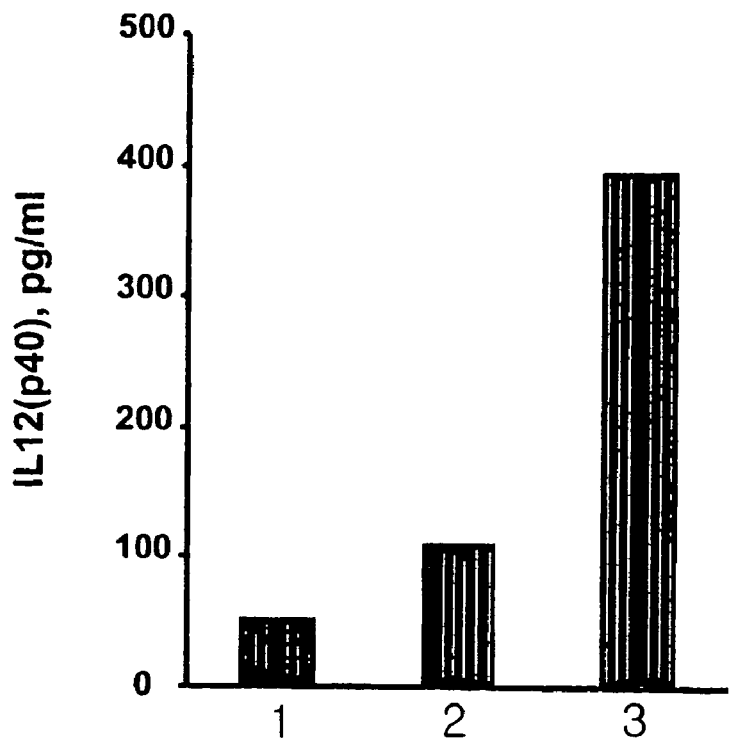
FIGS. 7A and 7B: ELISA(enzyme-linked immunosorbant assay) results showing IL-12(A) and IFN-γ (B) producing ability of CDs (1: the amount of protein produced after culturing for 1 week using GM-CSF; 2: the amount of protein produced after culturing for 1 week using GM-CSF, followed by culturing for 1 week using IFN-γ; and 3: the amount of protein produced after culturing for 1 week using GM-CSF and for 1 week using IFN-γ, followed by culturing for 1 day with added ionomycin.
Figure 7B:
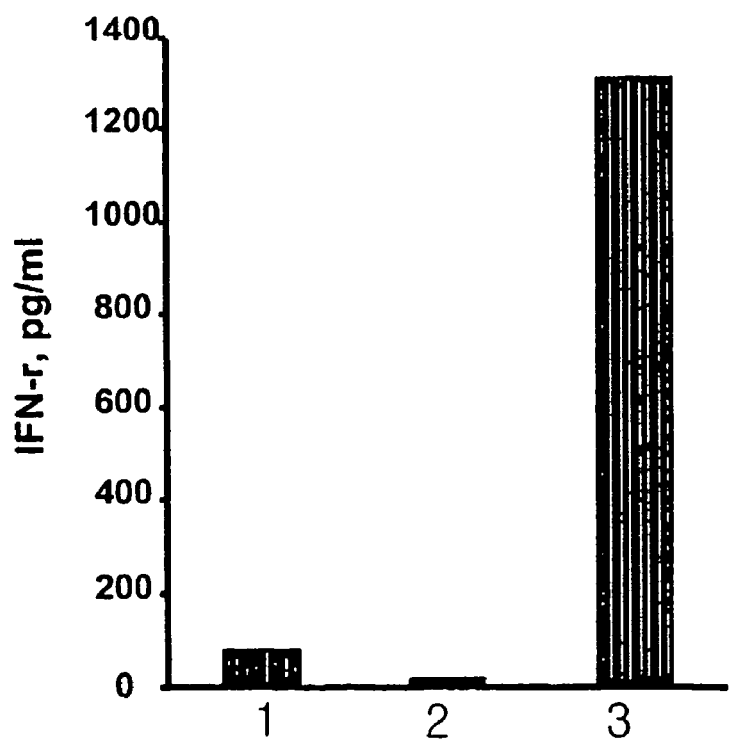

As the results in the FIGS. 7A and 7B show, the amounts of cytokines produced were very low until day 13, but jumped to high levels after ionomycin was added.

While the invention has been described with respect to the above specific embodiments, it should be recognized that various modifications and changes may be made to the invention by those skilled in the art which also fall within the scope of the invention as defined by the appended claims.

What is claimed is:

1. A method for differentiating a lymphoid dendritic cell of $CD8\alpha^+$ immunophenotype from human $CD34^+$ mononuclear cells separated from peripheral blood, which comprises the steps of culturing $1 \times 10^5$ /ml of the human $CD34^+$ mononuclear cells in two steps, first in a first medium consisting of 5% human serum albumin, 100 U/ml of penicillin, 100 ug/ml of streptomycin, 100 U/ml of L-glutamine and 50 ng/ml of GM-CSF for one week and then in a second medium consisting of 5% human serum albumin, 100 U/ml of penicillin, 100 ug/ml of streptomycin, 100 U/ml of L-glutamine and 200 U/ml of IFN-γ for one week.

2. The method of claim 1, which further comprises a step of adding 1 μg/ml of ionomycin to the second medium the day before the end of the second culture.

3. The method of claim 1, wherein the immunophenotype of the lymphoid dendritic cell is $CD1a^-$, $CD3^-$, $CD4^-$, $CD8\alpha^+$, $CD11c^+$, $CD14^-$, $CD40^+$, $CD54^+$, $CD80^+$, $CD83^+$, $CD86^+$, HLA-I$^+$ and HLA-II$^+$.

4. The method of claim 1, wherein the lymphoid dendritic cell is capable of inducing the production of interleukin-12 (IL-12) and interferon-γ (IFN-γ).

* * * * *